(12) United States Patent
Wall et al.

(10) Patent No.: US 9,402,805 B1
(45) Date of Patent: *Aug. 2, 2016

(54) METHOD OF TREATING MIDDLE EAR INFECTIONS

(71) Applicant: Alcon Pharmaceuticals Ltd., Fribourg (CH)

(72) Inventors: G. Michael Wall, Fort Worth, TX (US); Peter J. Conroy, Fort Worth, TX (US)

(73) Assignee: Alcon Pharmaceuticals Ltd., Fribourg (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/142,225

(22) Filed: Apr. 29, 2016

Related U.S. Application Data

(60) Continuation of application No. 14/838,637, filed on Aug. 28, 2015, now Pat. No. 9,345,714, which is a continuation of application No. 14/468,257, filed on Aug. 25, 2014, now Pat. No. 9,149,486, which is a continuation of application No. 12/357,697, filed on Feb. 13, 2009, now Pat. No. 8,846,650, which is a continuation of application No. 12/119,185, filed on May 12, 2008, now abandoned, which is a continuation of application No. 10/946,792, filed on Sep. 22, 2004, now abandoned, which is a division of application No. 10/243,341, filed on Sep. 13, 2002, now abandoned.

(60) Provisional application No. 60/323,951, filed on Sep. 21, 2001.

(51) Int. Cl.
| | |
|---|---|
| *A61K 31/573* | (2006.01) |
| *A61K 31/496* | (2006.01) |
| *A61K 9/00* | (2006.01) |

(52) U.S. Cl.
CPC .......... *A61K 9/0046* (2013.01); *A61K 31/496* (2013.01); *A61K 31/573* (2013.01)

(58) Field of Classification Search
CPC . A61K 31/573; A61K 31/496; A61K 31/495; A61K 31/545; A61K 31/56; A61K 31/57
USPC ........................................... 514/171, 253.08
See application file for complete search history.

(56) References Cited

U.S. PATENT DOCUMENTS

| | | | |
|---|---|---|---|
| 3,134,718 | A | 5/1964 | Nobile |
| 4,670,444 | A | 6/1987 | Grohe et al. |
| 4,686,214 | A | 8/1987 | Boltralik |
| 4,844,902 | A | 7/1989 | Grohe |
| 5,223,493 | A | 6/1993 | Boltralik |
| 5,420,120 | A | 5/1995 | Boltralik |
| 5,540,930 | A | 7/1996 | Guy et al. |
| 5,597,560 | A | 1/1997 | Bergamini et al. |
| 5,679,336 | A | 10/1997 | Ali et al. |
| 5,747,061 | A | 5/1998 | Amselem et al. |
| 5,843,930 | A | 12/1998 | Purwar et al. |
| 5,863,941 | A | 1/1999 | Liedtke |
| 6,284,804 | B1 | 9/2001 | Singh |
| 6,359,016 | B2 | 3/2002 | Singh et al. |
| 6,395,746 | B1 | 5/2002 | Cagle |
| 8,846,650 | B2 * | 9/2014 | Wall ............... A61K 9/0046 514/171 |
| 9,149,486 | B2 * | 10/2015 | Wall ............... A61K 9/0046 |
| 9,345,714 | B2 * | 5/2016 | Wall ............... A61K 9/0046 |

FOREIGN PATENT DOCUMENTS

| | | |
|---|---|---|
| EP | 0661055 | 7/1995 |
| EP | 0868919 | 10/1998 |
| ES | 2065846 | 8/1995 |
| WO | 90/01933 | 3/1990 |
| WO | 96/39146 | 12/1996 |
| WO | 00/18386 | 4/2000 |
| WO | 00/18387 | 4/2000 |
| WO | 00/18388 | 4/2000 |
| WO | 00/18404 | 4/2000 |
| WO | 01/22936 | 4/2001 |

OTHER PUBLICATIONS

Carlos et al: "Dtermination of plasma ciprofloxacin levels in children treated with 0.2% topical ciproflaxcin for tympanic perforation", Acta Otorinolaring Esp., 2000 pp. 97-99, vol. 51(2).

Kiris et al: "The efficacy of topical ciprofloxacin in the treatment of chronic suppurative otitis media", Ear, Nose & Throat Journal, 1998, pp. 904-909, vol. 77(11).

Florea, et al: "Effect of topical dexamethasone versus rimexolone on middle ear inflammation in experimental otitis media with effusion", Acta Oto-Larynogologica, 2006, p. 910-915, vol. 126.

Gaignage, et al: "Dexamethasone bovine pharmacokinetics", European Journal of Drug Metabolism and Pharmacokinetics, 1991, pp. 219-221, vol. 16, No. 3.

Langhoff, et al: "Relative immunosuppressive potency of various corticosteroids measured in vitro", European Journal of Clinical Pharmacology, 1983, pp. 459-462, vol. 25.

Leung, et al: "Disease management of atopic dermatitis: a practice parameter", Annals of Allergy, Asthma & Immunology, Sep. 1997, pp. 197-211, vol. 79.

Mutara, "Treatment of cochlear-tinnitus with dexamethasone infusion into the tympanic cavity as steroid targeting therapy", J. Saitama Med School, 1997, pp. 201-210, vol. 24.

Pudrith, et al: "Effect of topical glucocorticoid treatment in chinchilla model of lipopolysacchande induced otitis media with effusion", International Journal of Pediatric Otorhinolaryngology, 2010, pp. 1273-1275, vol. 74.

Yamada, "Experimental studies of topical antibacterial chemotherapy on sustained-release antibacterial agents in otorhinolaryngology", Medical Journal of nagoya City University, 1977, pp. 99-113, vol. 48, No. 4.

(Continued)

*Primary Examiner* — Jennifer M Kim
(74) *Attorney, Agent, or Firm* — Mark Flanigan

(57) ABSTRACT

Aqueous suspension formulations containing dexamethasone and ciprofloxacin are disclosed for the treatment of middle ear infections in human patients having an open tympanic membrane.

22 Claims, 2 Drawing Sheets

(56) References Cited

OTHER PUBLICATIONS

Alper, et al., "Treatment of Chronic Suppurative Otitis Media with Topical Tobramycin and Dexamethasone," Arch. Otolaryngology—Head & Neck Surgery, (2000), pp. 163-173, vol. 126.

Arnes, et al., "Otitis externa: clinical comparison of local ciprofloxacin versus local oxytetracycline, polymyxin B, hydrocortisone combination treatment," Current Medical Research and Opinion, (1993), pp. 182-186, vol. 13(3).

Bartzokas, et al., Infections: decision-making options in clinical practice: 14 Chronic suppurative otitis media, 1998, pp. 75-78, Bios Scientific Publishers.

Bluestone, et al., Otitis Media in Infants and Children, 3rd Edition, 2001, p. 79-101, W.B. Saunders Company, Philadelphia, PA.

Brown, et al., "Microbiology of Tracheal Granulation Tissue Associated with Silicone Airway Prosthesis," Annals of Otology, Rhinology & Laryngology, 1996, pp. 624-627, vol. 105(8).e.

Claros, et al., "Determination of plasma ciprofloxacin levels in children treated with 0.2% topical ciprofloxacin for tympanic perforation," Acta Otorinolaring Esp., 2000, pp. 97-99, vol. 51(2).

Deschepper, et al., "Local Treatment of External Otitis and Otitis Media: Role of the Quinolones," Acta Oto-Rhino-Laryngol (Belgium), 1994, pp. 67-70, vol. 48.

Dohar, et al., "Topical Ciprofloxacin/Dexamethasone Superior to Oral Amoxicillin/Clavulanic Acid in Acute Otitis media with Otorrhea Through Tympanostomy tubes," Pediatrics, 2006, pp. 561-569, vol. 118.

Dohar, et al., "Treatment of Chronic Suppurative Otitis Media with Topical Ciprofloxacin," Annals of Otology, Rhonology, and Laryngology, 1998, pp. 865-871, vol. 197 (10P +1).

Doshi, et al., "Preparation and Evaluation of New Eye-Drops Containing a Combination of Ciprofloxacin and Dexamethasone," Indian Drugs, 2000, pp. 190-195, vol. 37(4).

Engel, et al., "Effectiveness of Specific Antibiotic/Steroid Combinations for Therapy of Experimental Psuedomonas aeruginosa Keratitits," Current Eye Research, 1994, pp. 229-234.eu.

Epstein, et al., "Prevention of Early Otorrhea in Ventilation Tubes," Otolaryngology—Head and Neck Surgery, 1992, pp. 758-762, vol. 107(6).

Esposito, et al., "Topical and Oral Treatment of Chronic Otitis Media with Ciprofloxacin," Arch. Otolaryngol Head Neck Surg, 1990, pp. 557-559, vol. 116.

Esposito, et al., "Topical Ciprofloxacin vs. Intramuscular Gentamicin for Chronic Otitis Media," Arch. Otolaryngol Head Neck Surg., 1992, pp. 842-844, vol. 118.

Falser, et al., Antibacterial Treatment of Otitis and Sinusitis with Ciprofloxacin and Penicillin V—A Comparison, Infection, 1988, pp. S51-S54, vol. 16 (Supp. 1).

Force, et al., "Topcial Ciprofloxacin for Otorrhea after Tympanostomy Tube Placement," Arch. Otolaryngol, Head, Neck, Surg., 1995, pp. 880-884, vol. 121.

Fradis, et al., "Chronic Otitis Media Treated Topically with Ciprofloxacin or Tobramycin," Arch. Otolaryngol, Head, Neck, Surg., 1997, pp. 1057-1060, vol. 123.

Goldblatt, "Topical ofloxacin versus systemic amoxicillin/clavulanate in purulent otorrhea in children with tympanostomy tubes," International J. of Pediatric Otorhinolaryngology, 1998, pp. 91-101, vol. 46.

Hobden, et al., "Ciprofloxacin and Prednisolone Therapy for Experimental Pseudomonas Keratitis," Current Eye Research, 1992, pp. 259-266, vol. 11(3).

Hobden, et al., "Prednisolone Phosphate Concurrently Administered with Ciprofloxacin for the Therapy of Experimental Pseudomonas Aeruginosa Keratitis," Current Eye Research, 1993, pp. 469-473, vol. 12(5).

Isaacson, et al., "Care of the Child with Tympanostomy Tubes," Pediatric Otorhinolaryology, 1996, pp. 1183-1193, vol. 43(6).

Kasemsuwan, et al., "A double blind, prospective trial of topical ciprofloxacin versus normal saline solution in the treatment of otorrhoea," Clin. Otolaryngol, 1997, pp. 44-46, vol. 22.

Kay, et al., "Meta-analysis of tympanostomy tube sequelae," Otolaryngology—Head and Neck Surgery, 2001, pp. 374-380, vol. 124(4).

Kiris, et al., "The Efficacy of Topical Ciprofloxacin in the Treatment of Chronic Suppurative Otitis Media," Ear, Nose & Throat Journal, 1998, pp. 904-909, vol. 77(11).

Legent, et al., "Controlled Prospective Study of Oral Ciprofloxacin versus Amoxycillin/Clavulanic Acid in Chronic Suppurative Otitis Media in Adults," Chemotherapy, 1994, pp. 16-23, vol. 40 (Supp. 1).

Lorente, et al., "Multi-Centre Study Comparing the Efficacy and Tolerance of Topical Ciprofloxacin (0.3%) versus Topical Gentamicin (0.3%) in the Treatment of Simple, Non-Cholesteatomatous Chronic Otitis Media in the Suppurative Phase," Anales Iber-Amer, 1995, pp. 521-533, vol. XXII.

Mandel, et al., "Acute Otorrhea: Bacteriology of a Common Complication of Tympanostomy Tubes," Annals of Otology, Rhinology and Laryngology, 1994, pp. 713-718, vol. 103(9).

Mangat, et al., "T-tubes: a retrospective review of 1474 insertions over a 4-year period," Int. J. Pediatric Otorhinolaryngology, 1993, pp. 119-125, vol. 25.

Martinez, et al., "Antimicrobial Therapy in Chronic Suppurative Otitis Media," Acta Otorrinolaringol Esp., 1999, pp. 15-19, vol. 50(1).

Piccirillo, et al., "Ciprofloxacin for the Treatment of Chronic Ear Disease," Laryngoscope, 1989, pp. 510-513, vol. 99.

Pistorius, et al., "Prospective, Randomized, Comparative Trial of Ciprofloxacin Otic Drops, with or without Hydrocortisone, vs. Polymyxin B-Neomycin-Hyrocortisone Otic Suspension in the Treatment of Acute Difuse Otitis Externa," Infectious Diseases in Clinical Practice, 1999, pp. 387-395, vol. 8(8).

Podoshin, et al., "Local Treatment of Purulent Chronic Otitis Media with Ciprofloxacin," Harefuah, 1998, pp. 32-36, vol. 134(1).

Rodriguez, et al., "Efficacy of Topical Ciprofloxacin in the Treatment of Chronic Otorrhea," Acta Otorrinolaring Esp., 1995, pp. 15-18, vol. 46(1).

Rodriguez, et al., "Efficacy of Topical Ciprofloxacin in the Treatment of Ear Infections in Adults," J. Antimicrob. Chemotherapy, 1993, pp. 452-453, vol. 31.

Sabater, et al., "Prospective randomized double-blind study of the effectivenss and tolerance of topical ciprofloxacillin versus topical gentamicin in the treatment of simple chronic middle otitis and diffuse external otitis," Acta Otorhinolaringol Esp (Spain), 1996, pp. 217-220, vol. 47(3).

Shulman, et al., "Comparative evaluation of the short-term bactericidal potential of a steroid-antibiotic combination versus steroid in the treatment of chronic bacterial blepharitis and conjunctivitis," European J. of Ophthalmology, 1996, pp. 361-367, vol. 6(4).

Tutkun, et al., "Treatment of Chronic Ear Disease," Arch. Otolaryngol Head Neck Surg, 1995, pp. 1414-1416, vol. 121.

Tye, et al., "Otorrhea in Young Children after Tympanostomy-Tube Placement for Persistent Middle-Ear Effusion: Prevalence, Incidence, and Duration," Pediatrics, 2001, pp. 1251-1258, vol. 107(6).

Van De Heyning, et al., "Ciprofloxacin in Oral Treatment of Ear Infections," Pharmaceutisch Weekblad Scientific Edition, 1986, pp. 63-66, vol. 8.

Van De Heyning, et al., "Use of Ciprofloxacin in Chronic Suppurative Otitis," Rev. Infect. Dis., 1988, pp. S250-S251, vol. 10 (Suppl 1).

Wintermeyer, et al., "Efficacy of Ototopical Ciprofloxacin in Pediatric Patients with Otorrhea," Otalaryngol Head, Neck, Surg., 1997, pp. 450-453, vol. 116(4).

Ciloxan Product Information, Physicians' Desk Reference for Ophthalmology, pp. 209-211 (1998).

CIPRO HC OTIC, Physicians Desk Reference (2000).

Dexamethasone, Physicians Desk Reference (2000).

"Gentamicin ear drops: ototoxicity," WHO Drug Information, vol. 15(1), p. 20 (2001).

"Steroid and Antibiotic Solutions and Suspensions," Ophthalmic Drug Facts 1999, pp. 121-122 (1999).

* cited by examiner

METHOD OF TREATING MIDDLE EAR INFECTIONS

CROSS-REFERENCE TO RELATED APPLICATIONS

This application is a Continuation (CON) of co-pending U.S. application Ser. No. 14/838,637 filed Aug. 28, 2015; which is a Continuation of U.S. application Ser. No. 14/468,257 filed Aug. 25, 2014, now U.S. Pat. No. 9,149,486; which is a continuation of U.S. application Ser. No. 12/357,697 filed Feb. 13, 2009, now U.S. Pat. No. 8,846,650; which is a Continuation of Ser. No. 12/119,185 filed May 12, 2008 now abandoned; which is a Continuation of Ser. No. 10/946,792 filed Sep. 22, 2004 now abandoned; which is a Divisional of Ser. No. 10/243,341 filed Sep. 13, 2002 now abandoned, priority of which is claimed under 35 U.S.C. §120, the contents of which are incorporated herein by reference. This application also claims priority under 35 U.S.C. §119 to U.S. Provisional Application, Ser. No. 60/323,951, filed Sep. 21, 2001, the contents of which are incorporated herein by reference.

BACKGROUND OF THE INVENTION

This invention relates to the use of formulations of ciprofloxacin and dexamethasone to treat otic infections. Specifically, the invention relates to the topical use of such a fixed combination to treat middle ear infections in humans.

External ear infections, known as acute otitis externa ("AOE"), are currently treated with oral antibiotics, topical single-entity antibiotics, or topical antibiotic/steroid combination products. An example of an oral antibiotic product used to treat AOE is AUGMENTIN® (amoxicillin and clavulanic acid). An example of a single-entity antibiotic product approved for topical use in treating AOE is FLOXIN® (ofloxacin). Examples of combination products approved for this use include CORTISPORIN® (hydrocortisone, neomycin sulfate, and polymyxin b sulfate) and CIPRO®HC (ciprofloxacin and hydrocortisone). A product called SOFRADEX (gramicidin, framycetin and hydrocortisone) is available in some European countries and in Australia. External ear infections typically involve bacteria of the following types: *Pseudomonas aeruginosa, Staphylococcus aureus. Staphylococcus* sp. and *Coryneforms*.

In contrast, middle ear infections known as otitis media ("OM") typically involve bacteria of the following types: *S. pneumonia, H. influenzae* and *M. catarrhalis*. Patients with chronic or severe middle ear infections may have their ear drums (tympanic membranes) intentionally punctured and drainage tubes, often referred to as a tympanostomy tubes, implanted. In other cases, particularly in patients with severe OM, the tympanic membrane may rupture. Whether surgically punctured or accidentally ruptured, open tympanic membranes allow the bacteria characteristic of AOE and OM to mix.

Patients with OM are currently treated with oral antibiotics such as AUGMENTIN®. When drainage through an open tympanic membrane into the outer ear persists, either an oral antibiotic (e.g., AUGMENTIN®) or a topical antibiotic (e.g., FLOXIN®) is often prescribed. Additionally, topical antibiotic/steroid combination products approved for AOE have been used "off-label" in some cases to treat OM in patients with an open tympanic membrane, including CORTISPORIN®, CIPRO®HC, and TOBRADEX® (tobramycin and dexamethasone). To date, however, no topical antibiotic/steroid combination product has been approved by the Food and Drug Administration in the U.S. for the treatment of OM in patients with an open tympanic membrane.

Fixed combination products containing ciprofloxacin and dexamethasone are known. Although no such product is currently approved in the U.S., this combination is commercially available for ophthalmic use in certain countries in South America as Biomotil-D (Allergan Frumtost) and Cilodex (Alcon Laboratories). Although the use of ciprofloxacin/dexamethasone combinations for the treatment of ocular and/or otic infections has been disclosed in the scientific and patent literature (see, for example, Spanish Patent Application No. 2,065,846 A1 (Feb. 16, 1995), WO 90/01933 and U.S. Pat. No. 6,284,804), there has been no disclosure of the use of such a combination specifically for treating OM in patients with open tympanic membranes.

SUMMARY OF THE INVENTION

The present invention provides a method of topically treating OM in human patients who have open tympanic membranes. The method involves the topical application of a fixed combination of ciprofloxacin and dexamethasone as an aqueous suspension product. Although the dosing regimen may vary depending on the age and weight of the patient, as well as the severity of the infection, in most cases, the combination product would be applied twice a day. Each application would involve topically administering three or four drops into the ear canal, preferably pumping the tragus to force product through the opening in the tympanic membrane and to the site of the infection/inflammation in the middle ear.

Among other factors, the present invention is based on the finding that an aqueous combination of ciprofloxacin and dexamethasone was not statistically more effective than ciprofloxacin alone in the treatment of AOE, but was surprisingly statistically more effective that ciprofloxacin alone in the treatment of OM in patients with an open tympanic membrane. The fact that a contribution of elements for ciprofloxacin and dexamethasone could be demonstrated for only OM and not AOE was not predictable, nor was the fact that such a contribution of elements would be shown in OM.

DETAILED DESCRIPTION OF THE INVENTION

Figure 1:
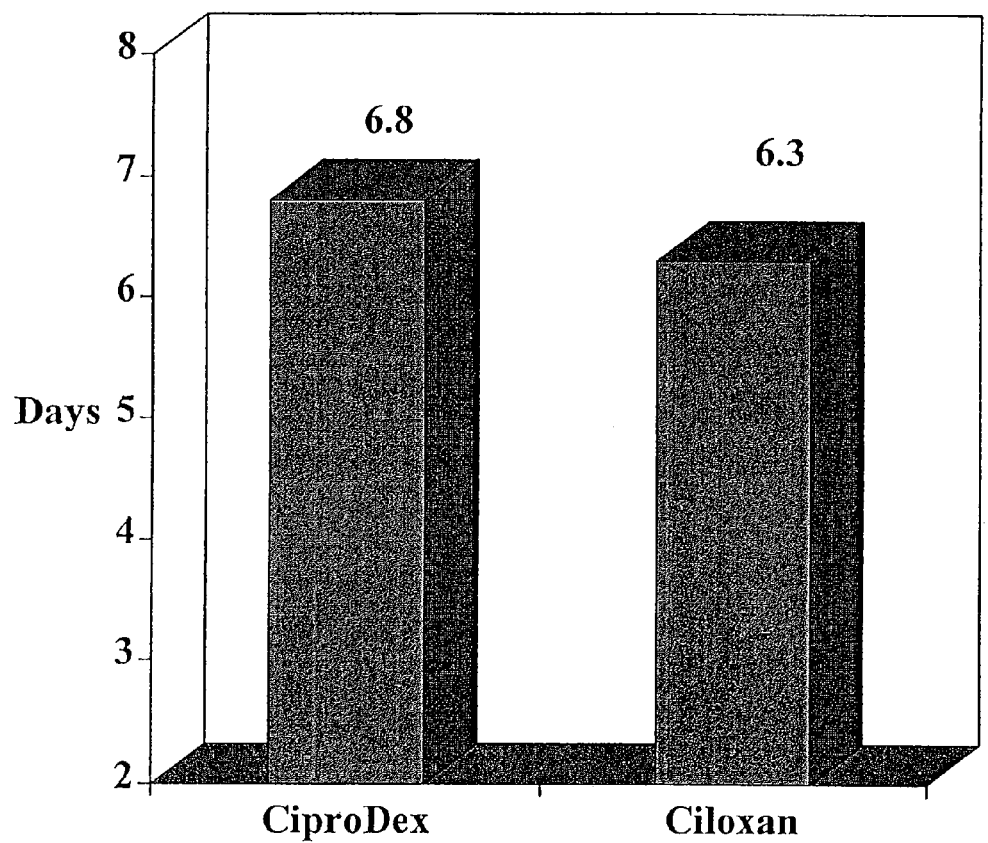
FIG. 1 shows the average number of days to time of cessation of ear pain in a human clinical study comparing a ciprofloxacin/dexamethasone combination product to a ciprofloxacin single-entity product.

Unless indicated otherwise, all ingredient amounts presented as a percentage are in units of weight %.

The methods of the present invention involve diagnosing a human patient as having OM and an open tympanic membrane. "Open tympanic membrane" means that the membrane has been intentionally punctured, with or without tympanostomy tube implantation, or has accidentally ruptured. Once diagnosed with OM and an open tympanic membrane, the method of the present invention involves topically administering to the ear canal of the patient's affected ear an aqueous suspension formulation of a fixed combination of ciprofloxacin and dexamethasone. OM includes, but is not limited to, acute otitis media and chronic supprative otitis media.

Dexamethasone can be present in any ophthalmically or otically acceptable form having poor water solubility such that the resulting formulation is a suspension formulation. Suitable forms of dexamethasone include dexamethasone alcohol (alcohol form of dexamethasone), dexamethasone acetate and dexamethasone phosphate. Dexamethasone alcohol is the preferred form of dexamethasone. The average particle size (mean volume basis) of the dexamethasone ingredient should be less than 10 μm to avoid irritation or discomfort. The average particle size is preferably less than 6 μm and most preferably less than 3 μm. Dexamethasone particles can be sized using known techniques, such as ball-milling, microfluidization and sonication. The ciprofloxacin ingredient can be any otically acceptable form such that the ciprofloxacin ingredient is in solution in the final formulation. A preferred form of ciprofloxacin is ciprofloxacin hydrochloride, monohydrate.

The dexamethasone ingredient will comprise about 0.01-0.5% and the ciprofloxacin ingredient will comprise about 0.1-0.4% of the aqueous suspension formulations administered according to the present invention. The preferred amounts of dexamethasone and ciprofloxacin in the formulations used in the present invention are 0.1% and 0.3%, respectively.

In addition to the active agents, the suspension formulations used in the present invention contain a tonicity agent. The tonicity agent may be ionic (e.g., NaCl) or nonionic (e.g., mannitol). The tonicity agent is preferably NaCl. The amount of NaCl will depend on the desired tonicity for the final formulation, but will generally range from 0.1-0.9%. The suspension formulations of the present invention preferably contain an amount of tonicity agent sufficient to cause the formulations to have an osmolality of about 250-350 mOsm.

The suspension formulations also contain a nonionic polymer as a suspending agent. Many otically acceptable nonionic polymers are known. These polymers include hydroxyethyl cellulose; hydroxypropylmethyl cellulose; methyl cellulose; carboxymethyl cellulose; polyvinyl pyrrolidone and polyvinyl alcohol. The preferred nonionic polymer is hydroxyethyl cellulose. The nonionic polymer will be present in the formulations of the present invention in an amount of about 0.1-0.5%. In the case of hydroxyethyl cellulose, the preferred concentration of nonionic polymer is 0.2%.

The formulations of the present invention also contain a nonionic surfactant in an amount from about 0.01-0.2%. Many otically acceptable nonionic surfactants are known. Suitable nonionic surfactants include tyloxapol; polyoxyethylene sorbitan esters, such as polysorbate 20, polysorbate 60, and polysorbate 80; polyethoxylated castor oils, such as Cremaphor EL; polyethoxylated hydrogenated castor oils, such as HCO-40; and poloxamers. The preferred surfactant is tyloxapol.

If desired, the formulations may contain a quaternary ammonium halide as a preservative. Suitable quaternary ammonium halides include polyquaternium-1 and benzalkonium halides. Preferred benzalkonium halides are benzalkonium chloride ("BAC") and benzalkonium bromide. In general, the amount of the preservative ingredient will range from about 0.005-0.3%. In the preferred case where the preservative is BAC, it is preferably present at a concentration of 0.01%.

If desired, a chelating agent may also be present in the suspension formulations used in the methods of the present invention. Suitable chelating agents include edetate disodium ("EDTA"); edetate trisodium; edetate tetrasodium; and diethyleneamine pentaacetate. Most preferred is EDTA. The chelating agent, if any, will typically be present in an amount from about 0.001-0.1%. In the case of EDTA, the chelating agent is preferably present at a concentration of 0.01%.

In the case of preserved or multi-dose formulations, the suspension formulations of the present invention may contain boric acid in an amount from 0.1-1.5%.

The formulations administered according to the present invention have a pH from 3-6, preferably 4.5. pH can be adjusted with NaOH/HCl. The preferred buffering system for these formulations is a combination of sodium acetate and acetic acid. The concentration of sodium acetate will generally range from 0.015-0.06%, and will preferably be about 0.03%. The concentration of acetic acid will generally range from 0.02-0.08, and will preferably be about 0.04%.

Though physicians may prescribe other dosing regimens depending on a number of factors including the severity of the OM, the age and weight of the patient, etc., the ciprofloxacin/dexamethasone combination products administered according to the present invention will generally be administered twice a day. Each administration will typically involve placing 3-4 drops (with a typical drop volume of 30-35 μL) of the suspension product in the affected ear. Preferably, the patient will pump the tragus of the affected ear to force the administered product through the opening in the tympanic membrane and to the site of the infection/inflammation in the middle ear.

In one embodiment, the present invention relates to a ciprofloxacin/dexamethasone aqueous suspension composition that is packaged with directions for use that indicate the composition may be used to treat otitis media in patients with an open tympanic membrane. As used herein, "directions for use" includes information contained in product labeling, package inserts and cartons or other packaging materials that accompany the ciprofloxacin/dexamethasone aqueous suspension composition of the present invention.

The following examples are intended to illustrate, but not limit, the present invention.

Example 1: Representative Formulations

| Ingredients | A % (w/w) | B % (w/w) | C % (w/w) | D % (w/w) | E % (w/w) |
|---|---|---|---|---|---|
| Ciprofloxacin HCl, Monohydrate | 0.35* | 0.35 | 0.35 | 0.35 | 0.35 |
| Dexamethasone Alcohol | 0.1 | 0.1 | 0.1 | 0.1 | 0.1 |
| Hydroxyethyl Cellulose | 0.2 | 0.2 | 0.2 | 0.2 | 0.2 |
| Benzalkonium Chloride | 0.01 | 0.01 | 0.01 | 0.01 | 0.01 |
| Sodium Acetate (Trihydrate) | 0.03 | 0.03 | 0.03 | 0.03 | 0.03 |
| Acetic Acid | 0.04 | 0.04 | 0.04 | 0.04 | 0.04 |
| Sodium Chloride | 0.25 | 0.25 | 0.80 | 0.53 | — |
| Edetate Disodium | 0.01 | 0.01 | 0.01 | 0.01 | 0.01 |
| Tyloxapol | 0.05 | 0.05 | 0.05 | 0.05 | 0.05 |
| Glycerin | 1.5 | — | — | — | 2.35 |
| Boric Acid | — | — | — | 0.6 | — |
| NaOH/HCl | q.s. pH 4.5 ± 0.2 | q.s. pH 4.5 ± 0.2 | q.s. pH 4.5 ± 0.2 | q.s. pH 4.5 ± 0.2 | q.s. pH 4.5 ± 0.2 |
| Purified Water | q.s. 100 | q.s. 100 | q.s.100 | q.s. 100 | q.s. 100 |
| Osmolality (mOsm) | 272 | 99 | 274 | 286 | 290 |

*equivalent to 0.3% ciprofloxacin base

Formulations A-E were made using the following method:
(1) For a formulation batch size of 500 ml, form a slurry by combining 75 g of 3 mm zirconium beads, 12 g of tyloxapol 1.0% stock solution and 0.5 g dexamethasone alcohol in a 30 ml polypropylene milling bottle (approx. 48% of the final batch requirement of tyloxapol is used);
(2) steam sterilize (autoclave) the slurry, including beads;

(3) aseptically ball mill the sterilized slurry for 18 hrs at 50 to 55 rpm;
(4) prepare an aqueous solution containing the remaining requirement of tyloxapol and the required amounts of all remaining ingredients (e.g., in the case of Formulation D, the remaining ingredients are ciprofloxacin hydrochloride monohydrate, benzalkonium chloride, sodium acetate, acetic acid, sodium chloride, hydroxyethylcellulose, boric acid, edetate disodium, and purified water;
(5) steam sterilize (autoclave) the aqueous solution prepared in step (4);
(6) combine the sterile slurry obtained in step 3 to the sterile solution obtained in step 5 by aseptically pouring the slurry through a sterile sieve (to remove the beads) into the solution obtained in step 5;
(7) adjust the formulation weight to 80-90% of batch weight using sterile-filtered purified water;
(8) check the final pH and adjust to pH 4.5±0.2 by sterile-filtered sodium hydroxide or hydrochloric acid, if needed; and
(9) bring the formulation to 100% of batch weight using sterile-filtered purified water.

An alternative method of preparing Formulations A-E, especially when the dexamethasone raw material is supplied or available already meeting the desired particle size specifications, is as follows:

(1) dry heat sterilize the dexamethasone raw material (recommended specification: between 7-11 hrs. at 130-140° C. (internal powder temperature);
(2) prepare a tyloxapol solution containing the batch requirement of tyloxapol in purified water;
(3) sterilize the tyloxapol solution by passing it through a 0.2 µm filter;
(4) aseptically combine the sterilized dexamethasone with the sterilized tyloxapol solution to form a sterile slurry and stir until homogenous;
(5) prepare an aqueous solution containing the required amounts of the remaining ingredients (e.g., in the case of Formulation D, the remaining ingredients are ciprofloxacin hydrochloride, monohydrate benzalkonium chloride, sodium acetate, acetic acid, sodium chloride, hydroxyethylcellulose, boric acid, edetate disodium and purified water;
(6) steam sterilize (autoclave) the aqueous solution prepared in step (5);
(7) aseptically combine the sterile slurry prepared in step (4) with the sterilized solution prepared in step (6);
(8) adjust the formulation weight to 80-90% of batch weight using sterile-filtered, purified water.
(9) check the final pH and adjust to pH 4.5±0.2 by sterile-filtered sodium hydroxide or hydrochloric acid, if needed; and
(10) bring the formulation to 100% of batch weight using sterile-filtered purified water.

Example 2

AOE Clinical Study in Human Patients

A clinical study with a primary objective of demonstrating superiority of a ciprofloxacin/dexamethasone combination product (ciprofloxacin 0.3%, dexamethasone 0.1%; Formulation D above) ("CIPRODEX") relative to the marketed CILOXAN® single-agent (ciprofloxacin 0.3%; Alcon Laboratories, Inc.) product for time to cessation of ear pain in patients with moderate to severe acute otitis externa (AOE) was conducted. A summary of the study details for this AOE study is provided below.

| Summary of AOE Study |
|---|
| CIPRODEX (Ciprofloxacin 0.3%) Suspension vs. CILOXAN (Ciprofloxacin 0.3%) Solution vs. CORTISPORIN Suspension (Neomycin 0.35%, Polymyxin B 10,000 IU/mL, Hydrocortisone 1.0%) for Topical Treatment of patients with moderate to severe Acute Otitis Externa (AOE). |

| | |
|---|---|
| Study Design: | Phase III multicenter, randomized, single-blind, active controlled, parallel group study. |
| Study Objectives: | Primary objectives of the study were to demonstrate: Superiority of CIPRODEX combination relative to CILOXAN single agent for time to cessation of ear pain. Therapeutic non-inferiority of CIPRODEX combination relative to CILOXAN single agent based on clinical response at the test of cure (TOC) visit (Day 18). Therapeutic non-inferiority of CIPRODEX combination relative to CORTISPORIN combination for clinical response at the TOC visit. Therapeutic non-inferiority of CILOXAN single agent relative to CORTISPORIN combination for clinical response at the TOC visit. |
| Patient Population: | A total of 909 patients enrolled into the study at 48 investigative sites in the United States between April 1998 and May 2000. |
| Inclusion Criteria: | Clinical diagnosis of moderate or severe AOE, at least one year of age, gave informed consent, and agreed to follow study procedures. |
| Posology: | Eligible patients were treated for 7 days with three drops BID CIPRODEX (n = 305), three drops BID CILOXAN (n = 305), or four drops TID CORTISPORIN (n = 299). |
| Study Visits: | Day 1, Day 3, Day 8 (End of Therapy, EOT), and Day 18 (TOC). |
| Clinical Evaluation: | Patient assessment of pain and tenderness using a daily diary. Physician evaluation of signs and symptoms of AOE, including inflammation, tenderness, edema, and otic discharge by visit. |
| Microbiology: | Microbiology outcomes were based on presumed or confirmed bacterial eradication. |
| Efficacy Criteria: | Cessation of ear pain was defined as the first day where the patient dairy pain score was zero, with no analgesics used in the prior 24 hours, and the ear pain score remained zero for all subsequent entries. Physician's assessment of clinical response of the patient at TOC on a 4-point scale (0 = cured, 1 = improved, 2 = no change, 3 = worse). |
| Safety Evaluation: | Based on the frequency and incidence of adverse events reported. |
| Overall Conclusions: | Time to cessation of pain is not different between CIPRODEX and CILOXAN treatments (i.e., no contribution of elements). CIPRODEX is non-inferior to CILOXAN for clinical cures and microbiological eradication. CIPRODEX produces more clinical cures than CORTISPORIN and is non-inferior for microbiological eradication. CILOXAN is superior to CORTISPORIN for clinical response in culture positive patients, and non-inferior for microbial eradication. CIPRODEX and CILOXAN are safe and well tolerated in pediatric and adult patients with AOE. |

Time to no pain was evaluated for CIPRODEX and CILOXAN, with the results shown in Table 1 and FIG. 1. These results show the average number of days to cessation of ear pain for the "modified intent-to-treat" ("MITT") population of the study. MITT is a term of art in the clinical sciences. For this study, the MITT population is defined as the population that received study drug, met inclusion criteria and was culture positive for bacteria on Day 1. The MITT population for this study comprised 267 patients for CIPRODEX and 261 patients for CILOXAN.

TABLE 1

| MITT: Time to No Pain (in days) | | |
|---|---|---|
| Treatment | Mean | Median |
| CIPRODEX | 6.8* | 5.0 |
| CILOXAN | 6.3 | 5.0 |

*p-value = 0.29 (Log-Rank Test; Kaplan-Meier Life Table Survival Estimates)

Data obtained in this AOE study demonstrate that time to cessation of ear pain was not different between CIPRODEX and CILOXAN, and therefore, no contribution of elements was shown for CIPRODEX. These results show a slight advantage for CILOXAN (6.8 days) over CIPRODEX (6.3 days) in average time to no otorrhea, but the differences were not statistically significant (p-value=0.29).

Example 3

OM with Open Tympanic Membrane Clinical Study in Human Patients

A clinical study with a primary objective of showing therapeutic superiority of CIPRODEX (Formulation D above) relative to CILOXAN for cessation of otorrhea (ear discharge) in tympanostomy tube patients with Acute Otitis Media (AOM) was conducted. A summary of the study details for this OM study is provided below.

Summary of AOM Study
Safety and Efficacy of Topical CIPRODEX (Ciprofloxacin 0.3%, Dexamethasone 0.1%) Suspension Compared to CILOXAN (Ciprofloxacin 0.3%) Solution in the Treatment of Acute Otitis Media with Tympanostomy Tubes (AOMT)

| | |
|---|---|
| Study Design: | Phase II multicenter, randomized, evaluator-blind, active controlledparallel group study. |
| Study Objectives: | The study objectives were to: Demonstrate therapeutic superiority of CIPRODEX combination relative to CILOXAN single agent for cessation of otorrhea, and to Evaluate the efficacy and safety of topical CIPRODEX Suspension in AOMT patients |
| Patient Population: | A total of 201 patients enrolled into the study at 21 investigative sites in the United States between March 2000 and January 2001. |
| Inclusion Criteria: | Pediatric patients (6 months to 12 years) with a patent tympanostomy tube and clinically diagnosed with acute otitis media with otorrhea that is visible by the parent/guardian of 3 weeks or less duration. |
| Posology: | Eligible patients were treated for 7 days with BID CIPRODEX (n = 103) or 7 days with BID CILOXAN (n = 98). |
| Study Visits: | Day 1, Day 3, Day 8 (End of Therapy, EOT), and Day 14 (Test of Cure, TOC). |
| Clinical Evaluation: | Twice daily patient assessment of cessation of otorrhea using a daily diary. Physician evaluation of signs and symptoms of AOMT, including presence of otorrhea,, characteristics of otorrhea, presence of granulation tissue tube patency, and overall clinical response by visit. |
| Microbiology: | Microbiology outcomes were based on presumed or confirmed bacterial eradication. |
| Efficacy Criteria: | Cessation of otorrhea was defined as ending on the first day on which the otorrhea is absent and remains absent for all subsequent diary entries. Physician's assessment of clinical response of the patient at TOC on a 4-point scale (0 = resolved, 1 = improved, 2 = no change, 3 = worse). |
| Safety Evaluation: | Based on the frequency and incidence of adverse events reported. |
| Overall Conclusions: | CIPRODEX has a statistically significantly shorter Time to Cessation of Otorrhea when compared to CILOXAN (using Log-Rank test of equality over strata). CIPRODEX is statistically significantly more effective than CILOXAN for Physician's Clinical Impression at the Day 3 Visit, but not at the Day 8 or Day 14 Visits (using Cochran-Mantel-Haenszel Rank Scores Test). No statistically significant differences were detected between CIPRODEX and CILOXAN for Microbiological Eradication Rates at the Test of Cure Visit (using Fisher's Exact Test). CIPRODEX and CILOXAN are safe and well tolerated in pediatric with AOMT. |

Figure 2:
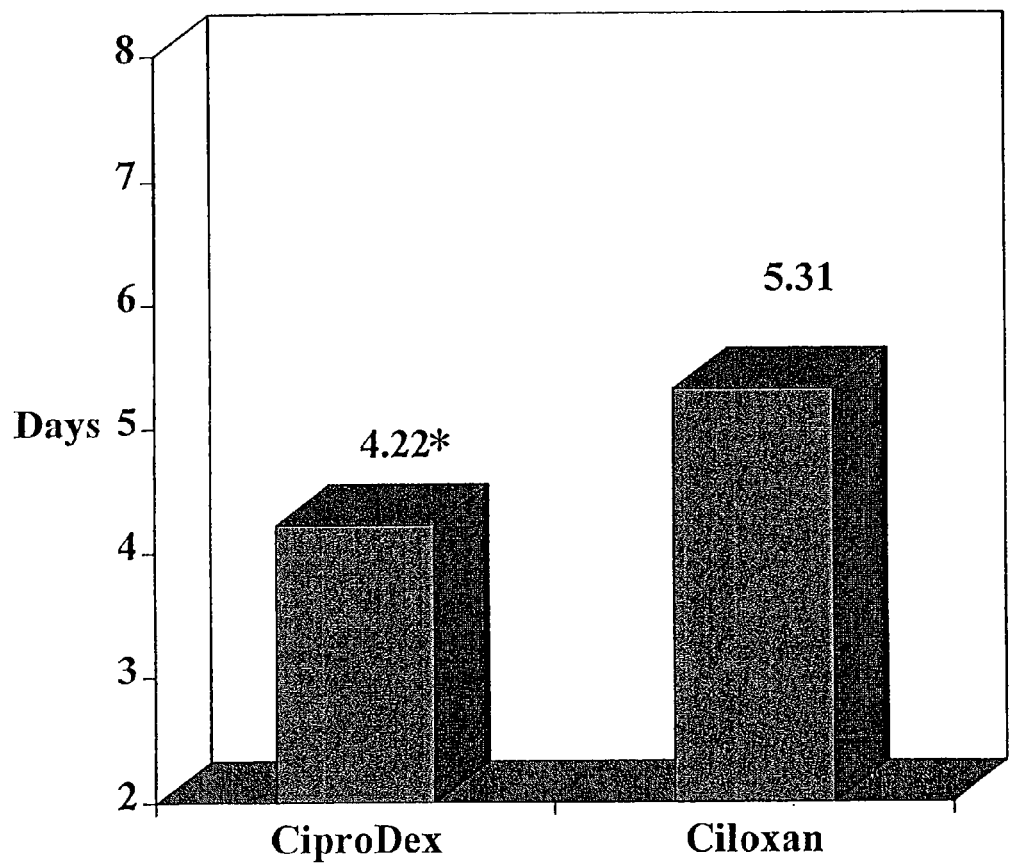
FIG. 2 shows the average number of days to cessation of otorrhea in a human clinical study comparing a ciprofloxacin/dexamethasone combination product to a ciprofloxacin single-entity product.

The results of this study for the MITT population are presented in Table 2 and FIG. 2. For this study, the MITT population is defined as the population that received study drug, met inclusion criteria, participated in at least one on-therapy visit, and was culture positive for bacteria on Day 1. The MITT population for this study comprised 87 patients for CIPRODEX and 80 patients for CILOXAN.

TABLE 2

| MITT: Time to No Otorrhea (in days) | | | | | | |
|---|---|---|---|---|---|---|
| Treatment | Mean | Median | Std. | N | Min. | Max. |
| CIPRODEX | 4.22* | 4 | 2.04 | 87 | 2 | 10 |
| CILOXAN | 5.31 | 5 | 1.94 | 80 | 2 | 10 |

*p-value = 0.0040 (Log-Rank test of equality over strata)

The results of this OM demonstrate a clinically and statistically significant difference in the time to cessation of otorrhea for CIPRODEX-treated patients (4.03 days) compared to CILOXAN-treated patients (5.06 days), approximately a 20% reduction in time to no otorrhea. In this study, contribution of elements for CIPRODEX was shown.

Example 4

CIPRODEX Vs. FLOXIN Study

A clinical study comparing CIPRODEX (Formulation D above) to FLOXIN in the treatment of tympanostomy tube patients with Acute Otitis Media (AOM) was conducted. A summary of the study details for this OM study is provided below.

Summary of CIPRODEX Vs. FLOXIN Study

Safety and Efficacy of Topical CIPRODEX Otic (Ciprofloxacin 0.3%/Dexamethason 0.1%) Suspension Compared to FLOXIN Otic (Ofloxacin 0.3%) Solution in the Treatment of Acute Otitis Media with Tympanostomy Tubes (AOMT)
Study Design:
Phase III, randomized, evaluator-masked, active-controlled, parallel-group study.
Objectives:
To demonstrate the non-inferiority of CIPRODEX Otic Suspension relative to FLOXIN Otic Solution in clinical and microbiological response at the test of cure (TOC) visit; and
To evaluate the efficacy and safety of CIPRODEX Otic Suspension for the treatment of patients with acute otitis media and otorrhea with tympanostomy tubes (AOMT).

Patient Population:

Approximately 500 pediatric patients with AOMT and post-tympanostomy tube otorrhea (250/arm) were planned. A total of 599 patients were enrolled.

Diagnosis and Main Criteria for Inclusion:

Pediatric patients, from 6 months to 12 years of age, with a patent tympanostomy tube, clinically diagnosed with acute otitis media and otorrhea of 3 weeks or less duration, visible by the parent/guardian, were enrolled.

Test Product, Dose and Mode of Administration, Batch Number(s):

CIPRODEX Otic (ciprofloxacin 0.3%/dexamethasone 0.1%) Suspension; topical otic administration of 4 drops into the infected ear(s) twice daily (BID) for 7 days.

Duration of Treatment:

Patients were required to undergo treatment for either seven (7) days if randomized to receive CIPRODEX or ten (10) days if randomized to receive FLOXIN.

Reference Therapy, Dose and Mode of Administration, Batch Number(s):

FLOXIN Otic (ofloxacin 0.3%) Solution; topical otic administration of 5 drops into the infected ear(s) twice daily (BID) for 10 days.

Criteria for Evaluation:

Subsequent to the demonstration of non-inferiority, superiority analyses were conducted. Analyses for the determination of superiority were based on the data set of patients who received treatment, had a positive pre-therapy culture and met the inclusion/exclusion criteria for enrollment (modified intent-to-treat, MITT). Analyses were also conducted for the intent-to-treat (ITT), per protocol (PP) and modified per protocol (MPP) data sets.

Efficacy:

The two primary variables were (1) the clinical response at the TOC visit; those patients rated as resolved/cured by the physicians based on a 4-point scale (0=resolved/cured, 1=improved, 2=not changed, 3=worsened); and (2) the microbiological response, success or failure, at the TOC visit for patients with positive pre-therapy cultures. Secondary efficacy variables were (1) the time to cessation of otorrhea as recorded in the patient diary; and as assessed by the physician's at each visit (2) the clinical response based on a 4-point scale (0=resolved/cured, 1=improved, 2=not changed, 3=worsened); (3) the granulation tissue based on a 4-point scale (0=none, 1=mild, 2=moderate and 3=severe); (4) the presence or absence of otorrhea; (5) the otorrhea volume based on a 4-point scale (0=absent, 1=scant, 2=moderate and 3=severe); and the color/type of otorrhea based on a 5-point scale (0=absent, 1=serous, 2=mucoid, 3=purulent, 4=sanguineous).

Safety:

The safety evaluation was conducted on all patients who were randomized into the study and received at least one dose of study drug. The safety analysis was based on the following; extent of exposure to study drug; adverse events; and audiometry examination.

Statistical Methods:

The statistical objective was to demonstrate the non-inferiority of CIPRODEX relative to FLOXIN in clinical and microbiological response at the TOC visit. Two-sided 95% confidence intervals for the difference between proportions between the two treatment groups were constructed. However, due to the lack of zero within the confidence limits, non-inferiority was demonstrated, and analyses allowed for a claim of superiority. Therefore, differences between the two treatments for clinical and microbiological response were evaluated using the Chi-square test of independence. For analyses of the secondary variables, the number and proportion of patients per response in each treatment group was presented and differences were assessed using LSMEANS (Mixed Model Analysis of Variance) or the Chi-square test of independence as appropriate. The log-rank test (Kaplan-Meier survival analysis was conducted to compare median time to cessation of otorrhea between the two treatments.

Summary—Conclusions:

CIPRODEX Otic Suspension is superior to FLOXIN Otic Solution in clinical and microbiological response at the test of cure (TOC) visit; and CIPRODEX Otic Suspension is effective and safe for the treatment of pediatric patients with acute otitis media and otorrhea with tympanosotomy tubes (AOMT).

These data demonstrate the superior effectiveness of CIPRODEX, an antibiotic-steroid combination drug, for the treatment of AOMT as shown in comparative analyses to a marketed product approved for the same indication.

This study evaluated the efficacy and safety of CIPRODEX, an antibiotic-steroid combination product (ciprofloxacin 0.3%/dexamethasone 0.1%) compared to FLOXIN, which contains antibiotic alone (ofloxacin 0.3%). The study duration was approximately three weeks long with four scheduled visits. Conditions between the treatment groups were identical except for the study drugs and the respective dosing regimens. Both drugs were topically administered BID, however, the FLOXIN group received 5 drops per dose for 10 days (per the package insert) and the CIPRODEX group, 4 drops per dose for 7 days. Outcome differences between the two groups are therefore attributed to the differences in treatment.

Efficacy Results:

A total of 599 patients were evaluable for the ITT analyses, 424 for the MITT, 460 for the PP and 357 for the MPP analyses. Of the ITT data set, 62% were male, 81% were Caucasian, 41% enrolled the right ear, 36% enrolled the left ear, and 23% enrolled both ears. The mean age was 2.45 years and the mean duration of the current episode of AOMT was 4.49 days in the right ear and 4.71 days in the left ear. In primary analyses, at the TOC visit, CIPRODEX was superior to FLOXIN for clinical cures for all data sets ($p \leq 0.0027$) and for microbiological eradication for MITT and MPP data sets ($p \leq 0.0061$). Additionally, for all data sets, CIPRODEX was superior to FLOXIN for treatment failure rate ($p \leq 0.0189$). In analyses of the secondary efficacy variables, CIPRODEX was superior to FLOXIN for time to cessation of otorrhea for all data sets ($p \leq 0.018$). Clinically, this translates to the cessation of otorrhea in 20 to 33% less time for the CIPRODEX treated patients in comparison to the FLOXIN treated patients (median time of 4 days for CIPRODEX versus 5-6 days for FLOXIN). For the remaining secondary efficacy variables, improvement in clinical response, absence of otorrhea, reduction in otorrhea volume and absence of otorrhea color, CIPRODEX was superior to FLOXIN at every study visit after baseline ($p \leq 0.0023$, $p \leq 0.0012$, $p \leq 0.0003$, and $p \leq 0.0003$, respectively). Moreover, at study visits Day 11 and Day 18, CIPRODEX was superior to FLOXIN for reduction in granulation tissue ($p=0.0086$ and $p=0.0383$, respectively). These outcomes demonstrate that CIPRODEX is not only a more effective treatment for AOMT in comparison to FLOXIN, but also results in a more rapid response to treatment and resolution of the clinical signs and symptoms of AOMT relative to FLOXIN. CIPRODEX is effective in treating acute otitis media with otorrhea in tympanostomy (AOMT) patients and results in 90% patients with clinical cure, 92% patients with microbiological success and a 4-day median time to cessation of otorrhea.

Efficacy Conclusions:
1. CIPRODEX is superior to FLOXIN for clinical cures at the TOC visit.

Clinical Cure Rates and 95% Confidence Intervals by Treatment Group (All Data Sets)

| | Treatment | | | | | | | | | | |
|---|---|---|---|---|---|---|---|---|---|---|---|
| | CIPRODEX Clinical Cure | | | | FLOXIN Clinical Cure | | | | | | |
| | No | | Yes | | No | | Yes | | | | |
| Data Set | N | % | N | % | N | % | N | % | Delta | Lower | Upper | P-value[a] |
| ITT | 75 | 25.25 | 222 | 74.75 | 117 | 38.74 | 185 | 61.26 | 13.49 | 6.10 | 20.88 | 0.0004 |
| MITT | 43 | 20.67 | 165 | 79.33 | 78 | 36.11 | 138 | 63.89 | 15.44 | 6.99 | 23.88 | 0.0004 |
| PP | 28 | 12.07 | 204 | 87.93 | 50 | 22.73 | 170 | 77.27 | 10.66 | 3.71 | 17.60 | 0.0027 |
| MPP | 18 | 10.00 | 162 | 90.00 | 37 | 21.76 | 133 | 78.24 | 11.76 | 4.17 | 19.36 | 0.0025 |

[a]Chi-square test of independence (Fisher's exact test when N < 5).

2. CIPRODEX is superior to FLOXIN for microbiological eradication at the TOC visit.

Microbiological Eradication Rates and 95% Confidence Intervals by Treatment Group (All Data Sets)

| | Treatment | | | | | | | | | | |
|---|---|---|---|---|---|---|---|---|---|---|---|
| | CIPRODEX Microbiological Eradication | | | | FLOXIN Microbiological Eradication | | | | | | |
| | No | | Yes | | No | | Yes | | | | |
| Data Set | N | % | N | % | N | % | N | % | Delta | Lower | Upper | P-value[a] |
| ITT | 128 | 43.10 | 169 | 56.90 | 154 | 50.99 | 148 | 49.01 | 7.90 | -0.07 | 15.87 | 0.0529 |
| MITT | 41 | 19.71 | 167 | 80.29 | 72 | 33.33 | 144 | 66.67 | 13.62 | 5.33 | 21.91 | 0.0015 |
| PP | 67 | 28.88 | 165 | 71.12 | 81 | 36.82 | 139 | 63.18 | 7.94 | -0.70 | 16.58 | 0.0722 |
| MPP | 15 | 8.33 | 165 | 91.67 | 31 | 18.24 | 139 | 81.76 | 9.90 | 2.83 | 16.97 | 0.0061 |

[a]Chi-square test of independence (Fisher's exact test when N < 5).

3. CIPRODEX is superior to FLOXIN for treatment failure rate.

Discontinuations Due to Treatment Failure by Treatment Group

| | Treatment | | | | | | | | |
|---|---|---|---|---|---|---|---|---|---|
| | CIPRODEX Treatment Failure | | | | FLOXIN Treatment Failure | | | | |
| | No | | Yes | | No | | Yes | | |
| Data Set | N | % | N | % | N | % | N | % | P-value[a] |
| ITT | 281 | 94.61 | 16 | 5.39 | 270 | 89.40 | 32 | 10.60 | 0.0189 |
| MITT | 199 | 95.67 | 9 | 4.33 | 192 | 88.89 | 24 | 11.11 | 0.0091 |
| PP | 220 | 94.83 | 12 | 5.17 | 188 | 85.45 | 32 | 14.55 | 0.0008 |
| MPP | 172 | 95.56 | 8 | 4.44 | 146 | 85.88 | 24 | 14.12 | 0.0017 |

[a]Chi-square test of independence (Fisher's exact test when N < 5).

4. CIPRODEX is superior to FLOXIN for improvement in clinical response at Days 3, 11 and 18.

Clinical Response by Treatment Group (MITT)

| | | Treatment | | | | |
|---|---|---|---|---|---|---|
| | | CIPRODEX | | FLOXIN | | |
| Visit | Clinical Response | N | % | N | % | P-value[a] |
| Day 3 | Missing | 1 | 0 | 0 | 0 | <.0001 |
| | Cured | 64 | 30.92 | 38 | 17.59 | |
| | Improved | 130 | 62.80 | 134 | 62.04 | |
| | Unchanged | 9 | 4.35 | 35 | 16.20 | |
| | Worse | 4 | 1.93 | 9 | 4.17 | |
| Day 11 | Missing | 1 | 0 | 0 | 0 | <.0001 |
| | Cured | 174 | 84.06 | 136 | 62.96 | |
| | Improved | 25 | 12.08 | 58 | 26.85 | |
| | Unchanged | 4 | 1.93 | 12 | 5.56 | |
| | Worse | 4 | 1.93 | 10 | 4.63 | |
| Day 18 | Missing | 1 | 0 | 0 | 0 | 0.0023 |
| | Cured | 174 | 84.06 | 153 | 70.83 | |
| | Improved | 20 | 9.66 | 38 | 17.59 | |
| | Unchanged | 6 | 2.90 | 12 | 5.56 | |
| | Worse | 7 | 3.38 | 13 | 6.02 | |

[a]Treatment difference from LSMEANS (Mixed Model Analysis of Variance).

5. CIPRODEX is superior to FLOXIN for time to cessation of otorrhea.

Time to Cessation of Otorrhea by Treatment Group (MITT)

|  | Treatment | | |
|---|---|---|---|
|  | CIPRODEX | FLOXIN | P-value[a] |
| Mean | 6.02 | 7.10 | 0.0204 |
| Median | 4.00 | 5.00 | |
| Std | 4.87 | 4.68 | |
| N | 208 | 216 | |
| Min | 2 | 2 | |
| Max | 21 | 21 | |

[a]Log-rank test (Kaplan-Meier survival analysis).

6. CIPRODEX is superior to FLOXIN for absence of otorrhea at Days 3, 11 and 18.

Presence/Absence of Otorrhea by Treatment Group (MITT)

|  |  | Treatment | | | | |
|---|---|---|---|---|---|---|
|  |  | CIPRODEX | | FLOXIN | | |
| Visit | Otorrhea | N | % | N | % | P-value[a] |
| Day 1 | Present | 208 | 100.00 | 216 | 100.00 | |
| Day 3 | Absent | 67 | 32.21 | 40 | 18.52 | 0.0012 |
|  | Present | 141 | 67.79 | 176 | 81.48 | |
| Day 11 | Absent | 176 | 84.62 | 137 | 63.43 | <.0001 |
|  | Present | 32 | 15.38 | 79 | 36.57 | |
| Day 18 | Missing | 1 | 0 | 0 | 0 | 0.0004 |
|  | Absent | 176 | 85.02 | 153 | 70.83 | |
|  | Present | 31 | 14.98 | 63 | 29.17 | |

[a]Chi-square test of independence (Fisher's exact test when N < 5).

7. CIPRODEX is superior to FLOXIN for reduction in granulation tissue at Days 11 and 18.

Granulation Tissue by Treatment Group (MITT)

|  |  | Treatment | | | | |
|---|---|---|---|---|---|---|
|  |  | CIPRODEX | | FLOXIN | | |
| Visit | Granulation Tissue | N | % | N | % | P-value[a] |
| Day 1 | Absent | 159 | 76.44 | 175 | 81.02 | 0.3449 |
|  | Mild | 30 | 14.42 | 21 | 9.72 | |
|  | Moderate | 15 | 7.21 | 16 | 7.41 | |
|  | Severe | 4 | 1.92 | 4 | 1.85 | |
| Day 3 | Missing | 1 | 0 | 0 | 0 | 0.3285 |
|  | Absent | 177 | 85.51 | 182 | 84.26 | |
|  | Mild | 24 | 11.59 | 22 | 10.19 | |
|  | Moderate | 6 | 2.90 | 10 | 4.63 | |
|  | Severe | 0 | 0.00 | 2 | 0.93 | |
| Day 11 | Missing | 1 | 0 | 0 | 0 | 0.0086 |
|  | Absent | 198 | 95.65 | 186 | 86.11 | |
|  | Mild | 8 | 3.86 | 22 | 10.19 | |
|  | Moderate | 1 | 0.48 | 8 | 3.70 | |
| Day 18 | Missing | 1 | 0 | 0 | 0 | 0.0383 |
|  | Absent | 203 | 98.07 | 192 | 88.89 | |
|  | Mild | 3 | 1.45 | 21 | 9.72 | |
|  | Moderate | 1 | 0.48 | 3 | 1.39 | |

[a]Treatment difference from LSMEANS (Mixed Model Analysis of Variance).

8. CIPRODEX is superior to FLOXIN for reduction in otorrhea volume at Days 3, 11 and 18.

Volume by Treatment Group (MITT)

|  |  | Treatment | | | | |
|---|---|---|---|---|---|---|
|  |  | CIPRODEX | | FLOXIN | | |
| Visit | Volume | N | % | N | % | P-value[a] |
| Day 1 | Scant | 17 | 8.17 | 14 | 6.48 | 0.3195 |
|  | Moderate | 104 | 50.00 | 99 | 45.83 | |
|  | Copious | 87 | 41.83 | 103 | 47.69 | |
| Day 3 | Missing | 1 | 0 | 0 | 0 | <.0001 |
|  | Absent | 66 | 31.88 | 39 | 18.06 | |
|  | Scant | 98 | 47.34 | 84 | 38.89 | |
|  | Moderate | 34 | 16.43 | 77 | 35.65 | |
|  | Copious | 9 | 4.35 | 16 | 7.41 | |
| Day 11 | Missing | 1 | 0 | 0 | 0 | <.0001 |
|  | Absent | 175 | 84.54 | 136 | 62.96 | |
|  | Scant | 19 | 9.18 | 42 | 19.44 | |
|  | Moderate | 7 | 3.38 | 26 | 12.04 | |
|  | Copious | 6 | 2.90 | 12 | 5.56 | |
| Day 18 | Missing | 2 | 0 | 0 | 0 | 0.0003 |
|  | Absent | 175 | 84.95 | 153 | 70.83 | |
|  | Scant | 14 | 6.80 | 21 | 9.72 | |
|  | Moderate | 8 | 3.88 | 27 | 12.50 | |
|  | Copious | 9 | 4.37 | 15 | 6.94 | |

[a]Treatment difference from LSMEANS (Mixed Model Analysis of Variance).

9. CIPRODEX is superior to FLOXIN for absence of otorrhea color and less purulent otorrhea at Day 3, and absence of otorrhea color and less mucoid otorrhea at Days 11 and 18.

Color/Type by Treatment Group (MITT)

|  |  | Treatment | | | | |
|---|---|---|---|---|---|---|
|  |  | CIPRODEX | | FLOXIN | | |
| Visit | Color/Type | N | % | N | % | P-value[a] |
| Day 1 | Absent | 0 | 0 | 0 | 0 | [b] |
|  | Serous | 21 | 60.00 | 14 | 40.00 | 0.2301 |
|  | Mucoid | 100 | 54.64 | 83 | 45.36 | 0.1417 |
|  | Purulent | 149 | 46.71 | 170 | 53.29 | 0.0607 |
|  | Sanguineous | 14 | 48.28 | 15 | 51.72 | 0.8335 |
| Day 3 | Absent | 67 | 63.21 | 39 | 36.79 | 0.0003 |
|  | Serous | 55 | 48.67 | 58 | 51.33 | 0.8593 |
|  | Mucoid | 63 | 43.75 | 81 | 56.25 | 0.2244 |
|  | Purulent | 36 | 38.71 | 57 | 61.29 | 0.0461 |
|  | Sanguineous | 1 | 14.29 | 6 | 85.71 | 0.1244 |
|  | Serous | 12 | 34.29 | 23 | 65.71 | 0.0770 |
|  | Mucoid | 7 | 15.91 | 37 | 84.09 | 0.0000 |
|  | Purulent | 14 | 40.00 | 21 | 60.00 | 0.2879 |
|  | Sanguineous | 0 | 0.00 | 3 | 100.00 | 0.2488 |
| Day 18 | Absent | 176 | 53.50 | 153 | 46.50 | 0.0002 |
|  | Serous | 8 | 44.44 | 10 | 55.56 | 0.7183 |
|  | Mucoid | 7 | 18.42 | 31 | 81.58 | 0.0001 |
|  | Purulent | 18 | 41.86 | 25 | 58.14 | 0.3510 |
|  | Sanguineous | 0 | 0.00 | 2 | 100.00 | 0.4992 |

[a]Chi-square test of independence (Fisher's exact test when N < 5).
[b]Could not be calculated.

Safety Results:

The safety of CIPRODEX and FLOXIN was evaluated in 599 pediatric patients with acute otitis media with tympanostomy tubes. No serious adverse events related to therapy were reported during this study. Seventy-eight patients (CIPRODEX: 32; FLOXIN: 46) were discontinued from the study due to adverse events, of which 76 were due to treatment-unrelated events. Adverse events in the overall safety population were all nonserious with the exception of three reports (abdominal pain, pneumonia, cellulitis), were generally mild to moderate, usually resolved with or without treatment, and generally did not interrupt patient continuation in the study. Similar types of otic and nonotic adverse events were noted in the infant and toddler population and the children population for CIPRODEX and FLOXIN. There were no trends observed in the analysis of adverse events according to age category either within or between CIPRODEX and FLOXIN treatment groups. Only three patients in the adolescent population were enrolled, and none of the adolescents reported adverse events.

Audiometry testing was performed to further assess the safety of CIPRODEX in the pediatric population. No clinically relevant or statistically significant (p=0.3863) difference in mean change of speech reception threshold (SRT) from baseline was observed between CIPRODEX and FLOXIN, and no clinically relevant decrease in hearing from baseline was observed with CIPRODEX or FLOXIN, based upon an assessment of bone and air conduction audiometry parameters.

CIPRODEX administered twice daily in the affected ear(s) is safe and well tolerated in pediatric patients with acute otitis media with tympanostomy tubes, based upon a review of adverse events and an assessment of audiometry parameters.

Safety Conclusions:

1. CIPRODEX administered twice daily in the affected ear(s) is safe and well tolerated in pediatric patients with acute otitis media with tympanostomy tubes, based upon a review of adverse events and an assessment of audiometry parameters.

2. Adverse events in the overall safety population were all nonserious with the exception of three reports (abdominal pain, pneumonia, cellulitis), were generally mild to moderate, usually resolved with or without treatment, and generally did not interrupt patient continuation in the study.

3. No clinically relevant or statistically significant difference in mean change of speech recognition threshold (SRT) from baseline was observed between CIPRODEX and FLOXIN.

4. No clinically relevant decrease in hearing from baseline was observed with CIPRODEX or FLOXIN, based upon an assessment of bone and air conduction audiometry parameters.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating a human patient comprising the steps of:
   (a) diagnosing the patient as having otitis media and an open tympanic membrane and/or having acute otitis externa in at least one ear; and
   (b) topically applying into the ear canal of the patients ear an aqueous suspension composition containing a combination of ciprofloxacin and dexamethasone, wherein the composition comprises a) 0.01-0.5% (wt.) dexamethasone; b) 0.1-0.4% (wt.) ciprofloxacin; c) 0.1-0.9% (wt.) tonicity agent; d) 0.01-0.2% (wt.) of a nonionic surfactant; and e) a buffer; wherein three or four drops of the aqueous suspension composition are administered to the patients ear twice a day, and wherein each drop is 30-35 µL.

2. The method of claim 1 wherein the dexamethasone is dexamethasone alcohol and the ciprofloxacin is ciprofloxacin hydrochloride, monohydrate.

3. The method of claim 1 wherein the aqueous suspension composition contains 0.1% (wt.) dexamethasone and 0.3% (wt.) ciprofloxacin.

4. The method of claim 1 wherein the dexamethasone has an average particle size on a mean volume basis of less than 3 µm.

5. The method of claim 1 wherein said tonicity agent is NaCl.

6. The method of claim 5 wherein said NaCl is present in an amount sufficient to cause the composition to have an osmolality of 250-350 mOsm.

7. The method of claim 1 wherein said nonionic surfactant is tyloxapol.

8. The method of claim 7 wherein said tyloxapol is present at a concentration of 0.05% (wt.).

9. The method of claim 1 wherein said aqueous suspension further comprises a suspending agent.

10. The method of claim 9 wherein said suspending agent is hydroxyethylcellulose.

11. The method of claim 10 wherein said hydroxyethylcellulose is present at a concentration of 0.2% (wt.).

12. The method of claim 1 wherein the aqueous suspension composition consists essentially of a) 0.1% (wt.) dexamethasone alcohol; b) 0.35% (wt.) ciprofloxacin hydrochloride, monohydrate; c) NaCl in an amount sufficient to cause the composition to have an osmolality of 250-350 mOsm; d) 0.2% (wt.) hydroxyethyl cellulose; e) 0.05% (wt.) tyloxapol; f) a buffer comprising sodium acetate and acetic acid; g) 0.01% (wt.) benzalkonium chloride; h) 0.01% (wt.) edetate disodium; i) 0.6% (wt.) boric acid; and wherein the composition has a pH of about 4.5.

13. The method of claim 1 wherein the method further comprises the step of pumping the tragus to force the aqueous suspension composition through the open tympanic membrane and into the middle ear.

14. The method of claim 1 wherein the otitis media is acute otitis media.

15. The method of claim 1 wherein the otitis media is chronic suppurative otitis media.

16. The method of claim 1 wherein the patient is a pediatric patient.

17. The method of claim 1 wherein the aqueous suspension composition containing a combination of ciprofloxacin and dexamethasone is packaged with directions for use that indicate the composition may be used to treat otitis media in patients with an open tympanic membrane.

18. The method of claim 1 wherein the aqueous suspension has a pH of 3-6.

19. The method of claim 1 wherein said treating comprises treating otorrhea associated with a middle ear infection.

20. The method of claim 1 wherein said treating comprises treating acute otitis externa associated with a middle ear infection.

21. The method of claim 1 wherein said treating comprises treating granulation tissue associated with a middle ear infection.

22. The method of claim 1 wherein four drops of said aqueous suspension composition are administered to the patients ear twice a day.

* * * * *